US008639488B2

(12) United States Patent  
Volker et al.

(10) Patent No.: US 8,639,488 B2  
(45) Date of Patent: Jan. 28, 2014

(54) ULTRASONIC MODELLING

(75) Inventors: Arno Willem Frederik Volker, Delft (NL); Arjan Mast, Rotterdam (NL); Joost Gerardus Petrus Bloom, Delft (NL); Pieter Jacobus Gijsbertus Van Beek, The Hague (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 418 days.

(21) Appl. No.: 12/992,486

(22) PCT Filed: May 13, 2009

(86) PCT No.: PCT/NL2009/050254  
§ 371 (c)(1),  
(2), (4) Date: Feb. 10, 2011

(87) PCT Pub. No.: WO2009/139627  
PCT Pub. Date: Nov. 19, 2009

(65) Prior Publication Data  
US 2011/0161065 A1   Jun. 30, 2011

(30) Foreign Application Priority Data

May 13, 2008  (EP) .................................... 08156074  
Sep. 12, 2008  (EP) .................................... 08164292

(51) Int. Cl.
| | |
|---|---|
| G06F 17/50 | (2006.01) |
| G06G 7/48 | (2006.01) |
| G06G 7/56 | (2006.01) |
| G01B 5/28 | (2006.01) |
| G01B 5/30 | (2006.01) |
| G01K 15/00 | (2006.01) |
| G01K 19/00 | (2006.01) |
| G01B 5/02 | (2006.01) |
| G01B 7/02 | (2006.01) |
| G01B 11/02 | (2006.01) |
| G01B 13/02 | (2006.01) |

(52) U.S. Cl.  
USPC .......... 703/14; 703/1; 703/5; 702/39; 702/99; 702/171

(58) Field of Classification Search  
USPC ........................ 703/14, 5, 1; 702/39, 99, 171  
See application file for complete search history.

(56) References Cited

U.S. PATENT DOCUMENTS

| | | | |
|---|---|---|---|
| 3,930,404 A | 1/1976 | Ryden, Jr. | |
| 5,063,780 A * | 11/1991 | Landry et al. | ................... 73/622 |
| 5,965,818 A | 10/1999 | Wang | |

(Continued)

FOREIGN PATENT DOCUMENTS

| | | |
|---|---|---|
| CN | 101014938 A | 8/2007 |
| CN | 101093170 A | 12/2007 |
| DE | 1 573 617 | 11/1970 |
| GB | 2 300 717 A | 11/1996 |
| WO | WO 2004/099764 A1 | 11/2004 |

(Continued)

OTHER PUBLICATIONS

Gret, Alexandre et al., "Time-Lapse Monitoring of Rock Properties with Coda Wave Interferometry", Mar. 9, 2006, Journal of Geophysical Research, vol. 111, American Geophysical Union.*

(Continued)

*Primary Examiner* — David Silver  
*Assistant Examiner* — Cedric D Johnson  
(74) *Attorney, Agent, or Firm* — Birch, Stewart, Kolasch & Birch, LLP

(57) ABSTRACT

A method of producing a temperature model of a surface of an object using ultrasonic transducers comprises the steps of iteratively adjusting a temperature model by using measured travel times of ultrasonic waves and their predictions model-based. The ultrasonic waves used for producing the temperature model are preferably substantially non-dispersive ultrasonic waves. The method may further involve a height model of the surface, which height model is produced using substantially dispersive ultrasonic waves and is corrected by using the temperature model.

19 Claims, 3 Drawing Sheets

(56) References Cited

U.S. PATENT DOCUMENTS

| 6,934,406 | B1 | 8/2005 | Nakano |
| 7,286,964 | B2 | 10/2007 | Kim |
| 2005/0075846 | A1* | 4/2005 | Kim ................................. 703/1 |

FOREIGN PATENT DOCUMENTS

| WO | WO 2005/010522 A2 | 2/2005 |
| WO | WO 2005010522 A2 * | 2/2005 |
| WO | WO 2007/068979 A1 | 6/2007 |

OTHER PUBLICATIONS

Lu, Yinghui et al. "A Methodology for Structural Health Monitoring with Diffuse Ultrasonic Waves in the Presence of Temperature Variations", Jun. 13, 2005, Ultrasonics 43, Elsevier B.V.*

Bond, Leonard J. et al., "Improved Assessment of Mass Concrete Dams Using Acoustic Travel Time Tomography. Part I—Theory", Jan. 6, 2000, Construction and Building Materials 14, Elsevier Science Ltd.*

Kupnik, Mario et al., "Numerical Simulation of Ultrasonic Transit-Time Flowmeter Performance in High Temperature Gas Flows", 2003, IEEE Ultrasonics Symposium, IEEE.*

Gan, Tat Hean et al., "Simultaneous Reconstruction of Flow and Temperature Cross-Sections in Gases using Acoustic Tomography", May 14, 2003, Acoustical Society of America.*

Tsai Wen-Yuan et al., "An Ultrasonic Air Temperature Measurement System with Self-Correction Function for Humidity", Jan. 21, 2005, Measurement of Science and Technology, 16, Institute of Physics Publishing, Ltd.*

* cited by examiner

ULTRASONIC MODELLING

BACKGROUND OF THE INVENTION

1. Field of the Invention

The present invention relates to ultrasonic modelling. More in particular, the present invention relates to a method and device for modelling the surface of an object, such as a pipe, using ultrasonic waves. The models produced with the present invention may comprise temperature models, height models, or both.

2. Background of the Invention

It is well known to use ultrasonic waves to obtain information on the surfaces of an object, for example a pole or pipe. Typically, ultrasonic pulses are transmitted towards the object, the reflected pulses are received and the travel times of the pulses are recorded. Any differences in travel times ("times-of-flight") of the pulses are indicative of differences in the relative height of the surface and hence of the wall thickness of the object. An example of this known technique is disclosed in U.S. Pat. No. 3,930,404.

U.S. Pat. No. 5,965,818 discloses a method using ultrasonic Lamb waves to measure reduction of wall thickness due to localised corrosion at pipe supports. Two transducers are used to make a Lamb wave travel along the pipe wall in the circumferential direction. By comparing measured time-of-flight data the change in time-of-flight due to corrosion can be quantified.

However, such known methods ignore the effects that temperature may have on ultrasonic measurements. Local temperature variations may cause refraction of the ultrasonic waves, as the propagation velocity of the waves may show variations between areas having different temperatures. Refractions cause delays, that is, longer travel times, which are also indicative of height differences. Accordingly, local temperature variations may be mistaken as height differences, thus causing errors in any height model of the surface.

U.S. Pat. No. 7,286,964 discloses a method of monitoring structural health conditions of objects by using acoustic waves, for example Lamb waves, and producing a tomographic image. This known method also involves determining an ambient temperature adjustment parameter. The adjustment is applied to the whole surface being monitored and is therefore not local. As a consequence, refraction due to local temperature variations is not compensated and measurement errors are likely to occur.

International Patent Application WO 2004/099764 discloses a method for determining structural features in a pipe, duct, container or other objects by using acoustic signals. The effects of temperature on the method are not mentioned in said document.

British Patent Application GB 2 300 717 discloses a method of modelling the temperature in segments of a pipeline. The liquid temperature and the ambient temperature are measured directly at several stations. Then the influence of kinetic energy, radiation and conduction are used to calculate the temperature in pipeline sections. The calculated section temperature is used to determine the net expansion and contraction of both the liquid and the pipeline. The spatial resolution of this known method is limited by the number of measuring stations and pipeline sections. The method will not be able to provide a circumferential temperature distribution of a pipeline section, nor a longitudinal temperature distribution having a high resolution.

SUMMARY OF THE INVENTION

It is an object of the present invention to overcome these and other problems of the Prior Art and to provide a method and device for producing a temperature model of a surface, which model is capable of indicating local temperature variations of the surface with an improved spatial resolution.

It is a further object of the present invention to provide a method and device for producing a temperature compensated height model of a surface.

Accordingly, the present invention provides a method of producing a temperature model of a surface of an object, the method being characterised by
  using ultrasonic transducers for producing and receiving substantially non-dispersive ultrasonic waves,
  iteratively adjusting a temperature model by using any discrepancies between measured travel times of the substantially non-dispersive ultrasonic waves over the surface and model-based predictions of said travel times, and
  the temperature model representing local temperatures of the surface.

By using substantially non-dispersive waves for producing the temperature model, the influence of the surface height (or pipe thickness) is virtually eliminated. As a result, any difference in travel times will substantially entirely be due to temperature differences.

By using a temperature model which represents local temperatures of the surface, detailed surface information can be provided, in contrast to Prior Art methods which produce only global temperature information. The present invention allows local temperatures to be determined of points on the surface which are less than one metre apart (for example only a few centimetres or decimetres apart), and also allows temperature differences in the circumferential direction of a pipe or drum to be determined.

The substantially non-dispersive waves preferably have a limited frequency range, or at least limited frequency ranges, to reduce or eliminate the influence of the frequency (wavelength) on the travel times. It is well known by those skilled in the art that dispersive waves decompose into constituents of different frequencies. As the velocity of ultrasonic waves travelling over surfaces is typically frequency-dependent, dispersive waves have the tendency to spread and thus to have less well-defined arrival times, unless dispersion correction is used. Non-dispersive waves do not tend to divide into constituent elements. However, it is difficult to generate fully non-dispersive waves and some dispersion may occur, unless the frequency band of the waves is kept narrow.

The present invention provides a method of producing a temperature model of a surface of an object using ultrasonic transducers, in which the temperature model preferably comprises a set of surface points, each surface point being indicative of the local temperature of the surface, and in which the travel times are preferably measured by transmitting ultrasonic waves from a first ultrasonic transducer to one or more second ultrasonic transducers, the first transducer and each second transducer defining a respective path along the surface.

By providing a temperature model comprising surface points indicative of the local temperature of the surface, it is possible to effectively model local temperatures and local temperature differences, each surface point representing a point on the surface. Accordingly, the temperature model of the present invention can be considered a temperature distribution model, indicative of the temperature distribution of the surface.

It is preferred that the steps of producing model-based predictions and adjusting are repeated until the discrepancies are smaller than a threshold, which threshold is preferably predetermined. By iteratively adjusting the temperature model, it is successively brought into conformity with the measured travel times. By using a threshold, the iterative procedure is terminated when sufficient accuracy has been achieved.

The method of the present invention preferably further comprises the step of tomographic inversion. This technique, which is well known per se, is very suitable for producing a model of the object's surface while using travel times of ultrasonic waves.

It is preferred that the ultrasonic waves are guided waves, in particular pulsed guided waves. It is further preferred that the pulsed waves are S0 mode (symmetric mode, zero order) waves, as S0 mode ultrasonic waves have been found to be very suitable for temperature modelling.

The method of the present invention may comprise the further step of detecting a surface point of which the temperature is lower than an average temperature minus a threshold value, the threshold value preferably being predetermined. In this way, local temperature extremes ("hot spots" and "cold spots") can be detected. In particular the detection of hot or cold spots, which may be caused by leaking liquids, allows holes in a pipe or in its cover to be detected.

Preferably, the average temperature is the average temperature of the whole surface. Alternatively, the average temperature may be that of part of the surface.

The present invention also provides a method of producing a height model of a surface of an object using ultrasonic transducers, the method comprising producing a temperature model of the surface of the object as defined above, the method further comprising the steps of:
- using the ultrasonic transducers for producing and receiving substantially dispersive ultrasonic waves, and
- iteratively adjusting a height model by using any discrepancies between measured travel times of the substantially dispersive ultrasonic waves over the surface and model-based predictions of said travel times.

Using the same ultrasonic transducers, both a temperature model and a height model may be produced. While for producing a temperature model substantially non-dispersive waves are preferred, substantially dispersive waves are preferred for producing a height model.

In the method of producing a height model is it further preferred that the height model comprises a set of surface points, each indicative of the local height of the surface, the method further comprising the steps of:
- predicting travel times based on the height model of the surface, and
- correcting the predicted travel times on the basis of the temperature model.

By correcting the height model using the temperature model, a more accurate height model is obtained.

More in particular, by correcting the predicted travel times of the height model on the basis of the temperature model, the height model is corrected for local temperature variations. In other words, the adjustment and final production of the height model takes the temperature model into account, thus compensating for any temperature effects, such as refraction due to temperature differences. Hence, the step of correcting the measured travel times on the basis of the temperature model preferably involves correcting for any refraction due to temperature gradients.

It is preferred that the temperature model and the height (or shape) model are produced consecutively, but in some embodiments the temperature and the height model may be produced substantially simultaneously.

It is further preferred that the steps of producing model-based predictions, correcting and adjusting are repeated until the discrepancies are smaller than a threshold, which threshold is preferably predetermined.

The temperature-adjusted height modelling method of the present invention may advantageously comprise the further step of applying, in addition to a temperature correction, a phase correction to the measured travel times of the substantially dispersive pulsed waves.

In an advantageous embodiment, the step of predicting travel times comprises the sub-step of interpolating the set of surface points in order to obtain an expanded set of surface points, the travel times being calculated using the expanded set.

The present invention additionally provides a computer program product for carrying out the data processing (for example, predicting, correcting, and/or adjusting) steps of the methods defined above. A computer program product may comprise a set of computer executable instructions stored on a data carrier, such as a CD or a DVD. The set of computer executable instructions, which allow a programmable computer to carry out the method as defined above, may also be available for downloading from a remote server, for example via the Internet.

The present invention further provides a device for modelling a surface of an object using ultrasonic transducers, the device comprising:
- a memory unit for storing a temperature model of the surface, the temperature model representing local temperatures of the surface,
- a transmission unit for transmitting substantially non-dispersive waves from a first transducer to one or more second transducers, and
- a processing unit arranged for iteratively adjusting a temperature model by using any discrepancies between measured travel times of the substantially non-dispersive ultrasonic waves over the surface and model-based predictions of said travel times.

In a preferred embodiment, the device according to the present invention may have the following advantageous features:
- the temperature model stored in the memory unit comprises a set of surface points, each surface point being indicative of the local temperature of the surface, and
- the processing unit is further arranged for:
  - measuring travel times of the pulsed waves,
  - predicting the travel times based on the temperature model of the surface,
  - adjusting the stored temperature model of the surface in response to any discrepancies between the measured travel times and the calculated travel times, and/or
  - repeating the steps of predicting and adjusting until the discrepancies are smaller than a threshold, which threshold is preferably predetermined.

As mentioned above, the present invention also envisages using both a temperature model and a height model of the surface. A further preferred embodiment of the device therefore has the following features:
- the memory unit is further arranged for storing a height model of the surface,
- the transmission unit is further arranged for transmitting substantially dispersive pulsed waves from the first transducer to the one or more second transducers, and
- the processing unit is further arranged for iteratively adjusting the height model by using any discrepancies between measured travel times of the substantially dispersive ultrasonic waves over the surface and model-based predictions of said travel times.

The device of the present invention offers the same advantages as the method discussed above.

The present invention still further provides a system for monitoring a pipeline or storage tank, comprising at least one first transducer, at least one second transducer and a device as defined above. The transducers and the device may advantageously being capable of communicating wirelessly.

BRIEF DESCRIPTION OF THE DRAWINGS

The present invention will further be explained below with reference to exemplary embodiments illustrated in the accompanying drawings, in which.

DETAILED DESCRIPTION OF THE PREFERRED EMBODIMENTS

Figure 1:
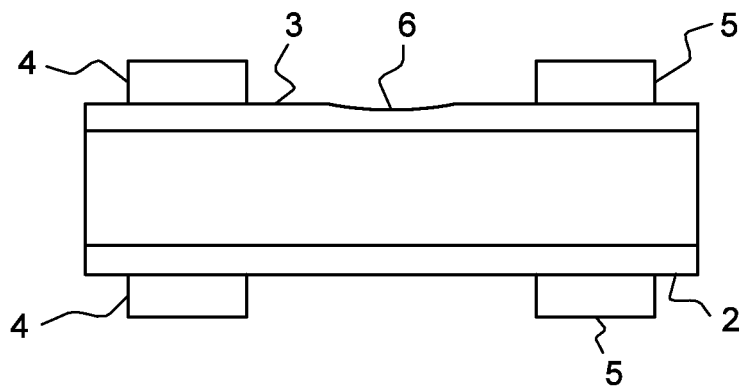
FIG. 1 schematically shows an object of which a surface is modelled in accordance with the present invention.

The pipe 2 shown merely by way of non-limiting example in FIG. 1 comprises a surface 3 which is to be modelled. In the example shown, the surface 3 has a recessed section 6 which may be caused by corrosion, for example. By suitably modelling the surface 3, the extent and (relative) height of the recessed section 6 may be determined.

First transducer units 4 and second transducer units 5 are mounted on the pipe 2, on either side of the surface 3. Although both the first and the second transducer units may be capable of transmitting and receiving ultrasonic waves, in the present invention the first transducer units 4 are used for transmitting ultrasonic pulsed waves while the second transducer units 5 are used for receiving these waves. The transducer units may be known per se and may be piezo-electric units.

Figure 2:
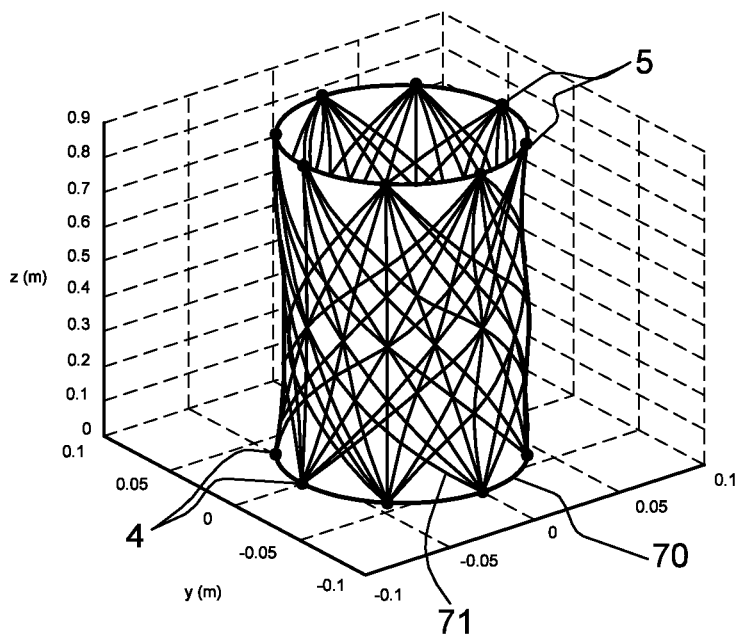
FIG. 2 schematically shows a 3-dimensional object model in accordance with the present invention.
Figure 3:
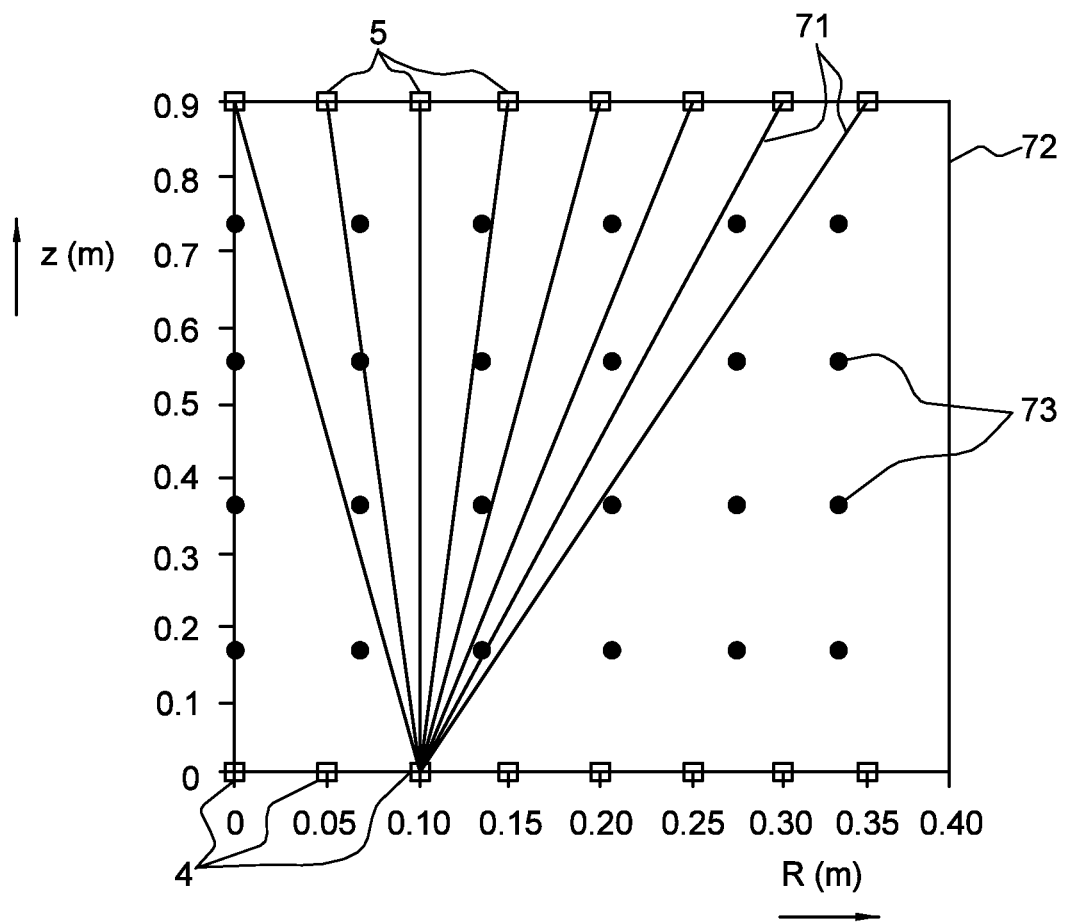
FIG. 3 schematically shows a 2-dimensional object model in accordance with the present invention.

The pulsed waves or pulses produced by the first transducers 4 have a defined duration of, for example, several μs (microseconds). The actual duration may depend on the particular application, for example the dimensions and mutual distances of the transducer units. The number of transducers may vary. At least one first transducer 4 and at least one second transducer 5 should be provided, although it is preferred to use multiple second transducers 5, for example two, three, four, eight of more second transducers 5. Using a plurality of second transducers 5 results in a plurality of paths travelled by the pulsed waves and hence an improved modelling of the surface. Similarly, it is preferred to use more than one first transducer 4. In the example of FIGS. 2 and 3, eight first transducers 4 and eight second transducers 5 are used, although the invention is not limited to these particular numbers. The transducers of a plurality of first and/or second transducers are preferably evenly spaced, although this is not essential.

An exemplary three-dimensional model is illustrated in FIG. 2, while the paths travelled by the pulsed waves and the reduction of surface points according to the present invention are illustrated by way of a two-dimensional model in FIG. 3. The three-dimensional model of FIG. 2 is based upon the two-dimensional model 72 of FIG. 3. Either model can be a temperature model or a height model.

The model 70 of FIG. 2 represents the (outer) surface of a pipe, for example the pipe 2 of FIG. 1. The x-axis and y-axis extend in a cross-sectional plane of the tubular model, while the z-axis extends in its longitudinal direction. The dimensions of this example are provided in meters (m). The three-dimensional model of FIG. 2 is in fact a reconstruction of the object 2 of FIG. 1. Three-dimensional reconstructions are known per se in the field of tomography.

The surface modelled in FIG. 2 extends between a set of first transducers 4 and a set of second transducers 5. Paths 71 extend between each of the first transducer 4 and each of the second transducers 5. The travel times of the pulses along these paths are proportional to the lengths of the paths. A path which extends along a smooth, straight surface will be shorter than a path crossing the recess 6 of FIG. 1. Accordingly, the travel times along these paths will differ and the pulses will arrive at different times.

The model will calculate (that is, predict) the arrival times of the pulses along the various paths. If the model initially assumes all paths to have equal lengths, a discrepancy between the measured travel times and the calculated travel times will occur for the paths crossing the recess 6. This discrepancy can be compensated by adjusting the model. Initial values of the model may be based upon measurements of the actual object (such as a pipe) and/or upon theoretical considerations.

In the two-dimensional example of FIG. 3, the horizontal axis extends along the circumference R of the tubular model, while the z-axis extends in its longitudinal direction. The dimensions are provided in meters (m).

As can be seen in FIG. 3, first transducers 4 and second transducers 5 are evenly spaced along the circumference of the model. Pulses produced by the first transducers will be detected by the second transducers. The arrival times, and hence the travel times, will correspond at least approximately to the set of paths 71 extending between each first transducer 4 and the second transducers 5. For the sake of clarity of the drawing, only one such set of paths 71 is shown in FIG. 3.

As explained above, the model contains information about the surface (3 in FIG. 1) of the object. In the case of a height model, this information may comprise a set of values representing the (relative or absolute) height of the surface in a number of points. Similarly, in the case of a temperature model, this information will typically comprise a set of values representing the (relative or absolute) temperature of the surface in a number of points ("sampling points").

As illustrated in FIG. 1, the surface height at the recess 6 is smaller than at the first transducer 4. In order to accurately model the surface, a large number of surface points are required, for example hundreds or even thousands of surface points. However, determining the surface points directly from the measured travel times would require a very large number of computations. For this reason, an embodiment of the invention provides a more efficient model which contains only a limited number of surface points, thus significantly reducing the number of computations.

In said embodiment, the model contains only a limited set of surface points 73. These "core" surface points are stored in the model and are adjusted if necessary to match the observed travel times. In the example shown, only 24 surface points are used in the model, thus providing a significant saving compared with the hundreds or thousands of points mentioned above. It will be understood that the number of "core" surface points may vary depending on the dimensions of the surface modelled and the accuracy required, and that this number may equally well be greater or smaller than 24, for example 16, 30 or 50. The number of "core" surface points of part of the model may be increased to provide a higher resolution in certain areas. Such a local increase of the number of "core" surface points may be dynamically adjusted.

In order to accurately model the surface and predict the travel times, a larger number of surface points are typically required. According to a further aspect of the present invention, an expanded set of surface points is obtained through interpolation. That is, the set of surface points of the model ("core" surface points) is interpolated to provide an expanded set of surface points used for calculating travel times and providing more detailed surface information, if required. In this way, the exemplary number of 24 surface points may be expanded to, for example, 1024 surface points.

The model used in said embodiment can therefore be considered a two-level model. On a basic level, a limited set of (for example 24) surface points is determined and stored. These "core" surface points are adjusted in accordance with the measured travel times. On a higher level, an expanded set of (for example 1024) surface points is determined by interpolation and (temporarily or permanently) stored. These "expansion" surface points are therefore derived indirectly from the measured travel times, unlike the "core" surface points which are derived directly.

Using the expanded set, the travel times according to the model can be accurately determined using numerical techniques which may be known per se. Typically, each path 71 is divided into a large number of sections. For each path, the travel times of all path sections is calculated, using the height information contained in the set of expanded surface points derived from the model. Then the travel time of each path is determined by adding the travel times of the sections of the particular path, resulting in the calculated travel times.

In most embodiments, the measured travel times are determined by subtracting transmission times of pulses from their arrival times. The transmission times are typically determined by recording the points in time at which an activation signal is sent to a first transducer unit, while the arrival times are typically determined by recording the points in time at which detection signals are received from the second transducer units.

Then the calculated (that is, predicted) travel times are compared with the measured travel times and any discrepancies are recorded. An optimisation procedure, which may be known per se, is then used to optimise the model(s) such that the discrepancies are removed. Suitable known optimisation procedures are the Levenberg-Marquardt and the Gauss-Newton procedures.

In the method of the present invention, surface waves may be used. Surface waves have the advantage that each pulse obtains information of a path, not just a point. It has been found that Rayleigh waves are very suitable surface waves as they follow the surface. As a result, their travel times provide very accurate information on the surface structure.

However, guided waves are preferred, in particular when not only information concerning the surface but also concerning the wall thickness of the object is required. In particular, the advantageous dispersive behaviour of guided waves is utilized: given the frequency, the propagation velocity of the waves depends on the wall thickness. Accordingly, any measured velocity changes are indicative of wall thickness variations, provided that the temperature of the object is uniform.

In accordance with the present invention, therefore, a temperature model is provided to model the temperature distribution of the object. The modelling is preferably carried out iteratively, adjusting an initial model in subsequent iterations until any difference between ultrasonic pulse travel times predicted by the model and actual measured ultrasonic travel times is smaller than a threshold value. This model allows to determine any travel time correction (or delay correction) caused by temperature differences, that is, by any non-uniform distribution of the temperature. Such temperature differences may cause refraction, and thus delays, and may result in inaccurate height measurements if not taken into account.

The temperature model production method of the present invention not only allows an accurate temperature model to be produced, but also allows a surface (height) modelling method to be improved by correcting any calculated and/or measured travel times using the temperature model. That is, any refraction due to local temperature differences can be taken into account to correct the measured and/or predicted travel times. As a result, the resulting height model is much more accurate.

The present invention produces two types of surface models: a temperature model representing the temperature distribution of the surface, and a height model representing the height of the surface (or, conversely, the thickness of the object). The temperature model can be used alone, to provide temperature information as such, but can also be used to correct the height model by taking any refraction delays into account (for example by determining the expected delay, caused by refraction, in a certain path of the ultrasonic waves, and subtracting this expected delay from the measured delay to determine a temperature compensated delay).

The present invention uses substantially non-dispersive (pulsed) waves to produce the temperature model, and substantially dispersive (pulsed) waves to produce the height (or thickness) model. This is based upon the insight that non-dispersive waves are not, or hardly, dependent on the thickness of the material (that is, on the height of the material). Any travel time differences will therefore be due to temperature variations (assuming that the frequency of the ultrasonic waves is constant). Dispersive waves, on the other hand, are dependent on the thickness of the material but also on the temperature (again assuming that the frequency is constant). By first determining the temperature effects using non-dispersive waves and then determining the height effects using dispersive waves and compensating for the temperature effects, very accurate height measurements, and therefore a very accurate height model may be obtained.

When using the S0 mode, non-dispersive and dispersive waves can easily be selected on the basis of their frequencies: the lower frequency ranges yield non-dispersive waves while higher frequency ranges result in dispersive waves.

According to a further aspect of the present invention, a phase correction may be used to correct dispersive waves. This is schematically illustrated in FIGS. 4A and 4B, where FIG. 4A shows an original pulse 81 (thick line) and its distorted counterpart 82 (thin line), while FIG. 4B shows a reconstructed pulse 83.

Figure 4A:
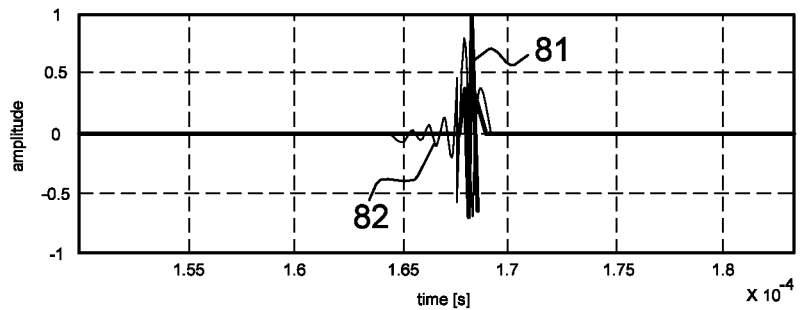
FIGS. 4A & 4B schematically show ultrasonic pulses used in the present invention.
Figure 4B:
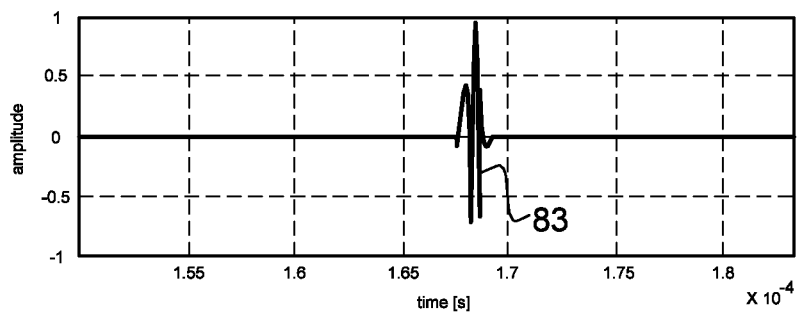

In FIG. 4A, a pulse 82 is shown to be distorted due to dispersion: the original phase relationship of the pulse is lost and the pulse is spread out in time, as compared to the original pulse 81. This makes the determination of the arrival time of the pulse, and hence its travel time, less accurate.

This loss of accuracy may be avoided by applying an (optional) phase correction X. In an exemplary embodiment, the phase correction X may be expressed as:

$$X = \exp^{-i\omega\left(\frac{x}{v(\omega_c)} - \frac{x}{v(\omega)}\right)}$$

where ω is the (angular) frequency, v(ω) is the frequency-dependent propagation velocity of the pulses, and x is the path length in the absence of any recesses or protrusions on the surface.

This correction may be applied by subjecting the distorted pulse 82 to a fast Fourier transform (FFT), multiplying the resulting spectrum by the phase correction X, and then applying an inverse fast Fourier transform (IFFT) to obtain the corrected pulse 83. After correction, the phase and hence shape of the pulse is restored, as illustrated in FIG. 4B. This restored pulsed wave 83 allows an accurate detection of its travel time. Those skilled in the art will realise that other phase correction techniques may be applied, for example using a predictive error filter.

Figure 5:
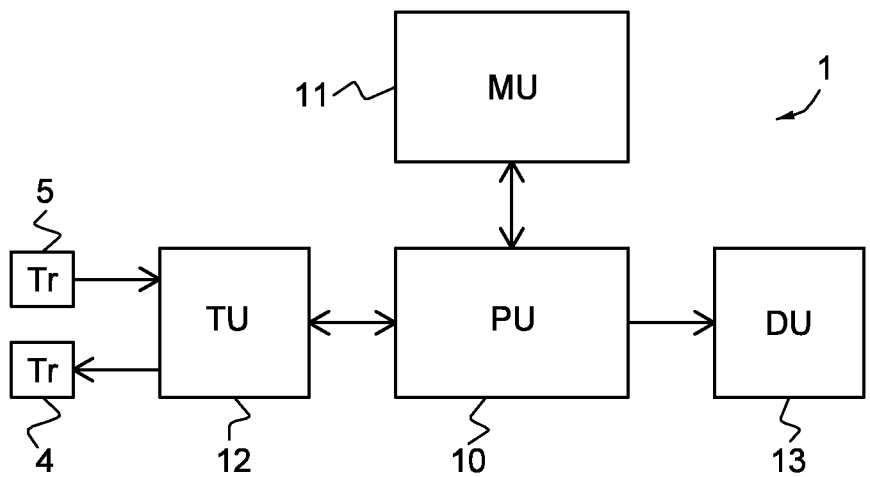
FIG. 5 schematically shows a surface modelling device according to the present invention.

A device for modelling a surface of an object is illustrated in FIG. 5. The device 1 comprises a processing unit (PU) 10, a memory unit (11), a transmission unit (TU) 12 and a display unit (DU) 13. The processing unit 10 preferably comprises a microprocessor capable of executing instructions of a software programme embodying the method of the present invention. The memory unit 11 may store this software programme, as well as parameters of the models, including the set of surface point values. The display unit 13 preferably comprises a display screen capable of displaying the models, in particular a reconstruction of the type illustrated in FIG. 2. The transmission unit 12 is capable of producing, under control of the processing unit 10, pulse transmission signals which are fed to the first transducer(s) 4. In addition, the transmission unit 12 is capable of receiving pulse detection signals produced by the second transducer(s) 5 and feeding suitable pulse detection information to the processing unit 10.

The transmission unit 12 may be arranged for wireless communication with the transducers 4 and 5, for example using radio frequency (RF) communication or infrared communication. The processing unit 10 may additionally be arranged for applying a phase correction as discussed above. Suitable programme steps for phase correction may be stored in the memory unit 11.

It will be understood that the invention is not limited to pipes or tubes but may also be applied on the surfaces or walls of other objects, for example (parts of) ship hulls, airplane fuselages, car bodies, tank armour, or other surfaces or wall structures, for example storage tanks, rods, steel bridges, and metal structures in buildings. It is noted that a combination of Rayleigh (pulsed) waves and guided (pulsed) waves may also be used.

The present invention is based upon the insight that ultrasonic waves may advantageously be used for producing a temperature model of a surface. The present invention benefits from the further insights that a temperature model may be used to correct a height model of a surface, and that non-dispersive waves are very suitable for producing a temperature model.

It is noted that any terms used in this document should not be construed so as to limit the scope of the present invention. In particular, the words "comprise(s)" and "comprising" are not meant to exclude any elements not specifically stated. Single (circuit) elements may be substituted with multiple (circuit) elements or with their equivalents.

It will be understood by those skilled in the art that the present invention is not limited to the embodiments illustrated above and that many modifications and additions may be made without departing from the scope of the invention as defined in the appending claims.

The invention claimed is:

1. A method of producing a temperature model of a surface of an object, the temperature model representing local temperatures of the surface, the method comprising:
   using a first ultrasonic transducer for producing substantially non-dispersive ultrasonic waves in the object at said surface, and using one or more second ultrasonic transducers for receiving the ultrasonic waves that have traveled through the object along the surface, wherein the ultrasonic waves travel along the surface and are received by the one or more second ultrasonic transducers;
   producing, by a processing unit, model-based predictions of said travel times based on the temperature model; and
   iteratively adjusting, by the processing unit, the temperature model by using any discrepancies between measured travel times of the substantially non-dispersive ultrasonic waves over the surface and the model-based predictions of said travel times.

2. The method according to claim 1, wherein the temperature model comprises a set of surface points, each surface point being indicative of the local temperature of the surface at a respective point on the surface, and wherein the travel times are measured by transmitting ultrasonic waves from a first ultrasonic transducer to one or more second ultrasonic transducers, the first transducer and each second transducer defining a respective path along the surface.

3. The method according to claim 1, wherein the processing unit repeats the steps of producing model-based predictions and adjusting until the discrepancies are smaller than a predetermined threshold.

4. The method according to claim 1, further comprising performing, by the processing unit, tomographic inversion.

5. The method according to claim 1, wherein the ultrasonic waves are guided waves.

6. The method according to claim 1, further comprising detecting, by the processing unit, a surface point of which the temperature is lower than an average temperature minus a predetermined threshold value.

7. The method according to claim 6, wherein the average temperature is the average temperature of the whole surface.

8. The method according to claim 1, wherein the step of producing model-based predictions of travel times comprises a sub-step of interpolating a set of surface points in order to obtain an expanded set of surface points, the travel times being calculated using the expanded set.

9. A non-transitory computer-readable medium containing a computer program product comprising computer-executable instructions for carrying out the producing step and the iteratively adjusting step according to claim 1.

10. A method of producing a height model of a surface of an object using ultrasonic transducers, the method comprising:
    producing, by the processing unit, the temperature model of the surface of the object according to claim 1,
    using the ultrasonic transducers for producing and receiving substantially dispersive ultrasonic waves, and
    iteratively adjusting, by the processing unit, a height model by using any discrepancies between measured travel times of the substantially dispersive ultrasonic waves over the surface and model-based predictions of said travel times.

11. The method according to claim 10, wherein the height model comprises a set of surface points, each indicative of a local height of the surface, the method further comprising the steps of:

predicting, by the processing unit, travel times based on the height model of the surface, and correcting, by the processing unit, the predicted travel times on the basis of the temperature model.

12. The method according to claim 11, wherein the processing unit repeats the steps of producing model-based predictions, correcting and adjusting until the discrepancies are smaller than a predetermined threshold.

13. The method according to claim 11, wherein the processing unit corrects for any refraction due to temperature gradients in the step of correcting travel times on the basis of the temperature model.

14. The method according to claim 11, further comprising applying, by the processing unit, in addition to a temperature correction, a phase correction to the measured travel times of the substantially dispersive waves.

15. A device for modeling a surface of an object using ultrasonic transducers, the device comprising:
- a memory unit for storing a temperature model of the surface, the temperature model representing local temperatures of the surface;
- a transmission unit for transmitting substantially non-dispersive waves from a first transducer to one or more second transducers;
- a processing unit arranged for iteratively adjusting a temperature model by using any discrepancies between measured travel times of the substantially non-dispersive ultrasonic waves over the surface and model-based predictions of said travel times;
- wherein said waves are pulsed waves;
- the temperature model stored in the memory unit comprises a set of surface points, each surface point being indicative of the local temperature of the surface at a respective point on the surface; and the processing unit is further arranged for:
- measuring travel times of the pulsed waves;
- predicting the travel times based on the temperature model of the surface;
- adjusting the stored temperature model of the surface in response to any discrepancies between the measured travel times and the model-based predictions of said travel times; and/or repeating the steps of predicting and adjusting until the discrepancies are smaller than a predetermined threshold.

16. The device according to claim 15, wherein:
- the memory unit is further arranged for storing a height model of the surface,
- the transmission unit is further arranged for transmitting substantially dispersive pulsed waves from the first transducer to the one or more second transducers, and
- the processing unit is further arranged for iteratively adjusting the height model by using any discrepancies between measured travel times of the substantially dispersive ultrasonic waves over the surface and model-based predictions of said travel times.

17. The device according to claim 16, wherein the height model comprising a set of surface points, each surface point being indicative of the local height of the surface.

18. A system for monitoring a pipeline or storage tank, comprising at least one first transducer, at least one second transducer and a device according to claim 15.

19. The system according to claim 18, wherein the device and the transducers are capable of communicating wirelessly.

* * * * *

UNITED STATES PATENT AND TRADEMARK OFFICE
CERTIFICATE OF CORRECTION

PATENT NO. : 8,639,488 B2  Page 1 of 1
APPLICATION NO. : 12/992486
DATED : January 28, 2014
INVENTOR(S) : Volker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 8,639,488 B2 |
| APPLICATION NO. | : 12/992486 |
| DATED | : January 28, 2014 |
| INVENTOR(S) | : Volker et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this
Twenty-ninth Day of September, 2015

Michelle K. Lee
*Director of the United States Patent and Trademark Office*